(12) United States Patent
Van Eperen et al.

(10) Patent No.: US 6,776,316 B2
(45) Date of Patent: *Aug. 17, 2004

(54) METHOD OF TUCKING REFASTENABLE SIDE SEAMS

(75) Inventors: David James Van Eperen, Appleton, WI (US); Steven James Langolf, Fon du Lac, WI (US); Steven L. Schnasse, New London, WI (US); Kent Allan Franklin, Appleton, WI (US); David Michael Lehner, Appleton, WI (US); Jesse Paul Sorenson, Little Chute, WI (US); Rodney Steele Gardinier, Appleton, WI (US); David Michael Clemens, Keller, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 207 days.

This patent is subject to a terminal disclaimer.

(21) Appl. No.: 09/966,793

(22) Filed: Sep. 28, 2001

(65) Prior Publication Data

US 2003/0062113 A1 Apr. 3, 2003

(51) Int. Cl.[7] .............................................. A41H 33/00
(52) U.S. Cl. ........................................... 223/37; 223/38
(58) Field of Search ................... 223/37, 38; 156/227, 156/443, 285, 164, 229

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,905,592 A | 9/1975 | Spencer et al. | |
| 3,984,272 A | 10/1976 | Teed | |
| 3,998,447 A | 12/1976 | Joa | |
| 4,022,456 A | 5/1977 | Hooper et al. | |
| 4,081,301 A | 3/1978 | Buell | |
| 4,205,679 A | 6/1980 | Repke et al. | |
| 4,340,563 A | 7/1982 | Appel et al. | |
| 4,523,671 A | 6/1985 | Campbell | |
| 4,610,680 A | 9/1986 | LaFleur | |
| 4,614,512 A | 9/1986 | Capdeboscq | |
| 4,615,695 A | 10/1986 | Cooper | |
| 4,663,220 A | 5/1987 | Wisneski et al. | |
| 4,665,306 A | 5/1987 | Roland et al. | |

(List continued on next page.)

FOREIGN PATENT DOCUMENTS

| | | | |
|---|---|---|---|
| AU | 78532/75 | 8/1976 | |
| EP | 217 032 | 2/1992 | |
| EP | 631 766 | 1/1995 | |
| FR | 2209368 | 6/1974 | |
| FR | 2219636 | 9/1974 | |
| GB | 2245149 | 1/1992 | |
| JP | 9-131364 A * | 5/1997 | |
| JP | 09131364 | 5/1997 | ............. A61F/5/44 |
| WO | WO 00/35398 | 6/2000 | |
| WO | WO 00/37009 | 6/2000 | |

*Primary Examiner*—Jeff H. Aftergut
(74) *Attorney, Agent, or Firm*—Pauley Petersen & Erickson

(57) ABSTRACT

A method of tucking a pair of refastenable side seams into a body portion of a pant-like garment in which the fold locations can be controlled and the likelihood of creases occurring in the fastening components is reduced or eliminated. The garment is positioned either on one vacuum conveyor or between an upper vacuum conveyor and a lower vacuum conveyor. Vacuum zones from the conveyors hold the garment in place. While the garment is held by the vacuum zones, the refastenable side seams are pushed between the front and back regions toward one another with the fastening components being placed in a flat configuration.

22 Claims, 12 Drawing Sheets

U.S. PATENT DOCUMENTS

| | | |
|---|---|---|
| 4,704,116 A | 11/1987 | Enloe |
| 4,739,910 A * | 4/1988 | Westphal et al. ............ 493/313 |
| 4,938,757 A | 7/1990 | Van Gompel et al. |
| 4,940,464 A | 7/1990 | Van Gompel et al. |
| 5,040,783 A | 8/1991 | Ruehl |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,300,007 A | 4/1994 | Kober |
| 5,492,591 A | 2/1996 | Herrmann et al. |
| 5,537,806 A | 7/1996 | Grierson et al. |
| 5,714,027 A | 2/1998 | Taub |
| 5,788,805 A | 8/1998 | Herrmann |
| 5,855,574 A | 1/1999 | Kling et al. |
| 5,897,291 A | 4/1999 | Gerwe et al. |
| 5,897,292 A | 4/1999 | Gerwe et al. |
| 5,904,802 A | 5/1999 | Niedermeyer |
| 6,017,406 A | 1/2000 | Vogt |
| 6,036,805 A | 3/2000 | McNichols |
| 6,079,562 A | 6/2000 | Bauer et al. |
| 6,139,004 A | 10/2000 | Couillard et al. |
| 6,250,357 B1 | 6/2001 | Niedermeyer |
| 6,254,714 B1 | 7/2001 | Niedermeyer |
| 6,287,287 B1 | 9/2001 | Elsberg |
| 6,461,344 B1 | 10/2002 | Widlund et al. |

* cited by examiner

METHOD OF TUCKING REFASTENABLE SIDE SEAMS

BACKGROUND OF THE INVENTION

This invention is directed to a method of tucking refastenable side seams into a main body of a pant-like garment while preventing creases in the refastenable seams, and maintaining control over the fold locations.

Pant-like absorbent garments, such as adult incontinence wear, infant and children's diapers, swim wear and training pants, typically have adhesive or mechanical fasteners on the sides for donning and removal, or else rely on a stretchable waist opening and leg openings to slide on and off the wearer. Absorbent garments that slide on and off a wearer can be messy after use. Furthermore, in order to remove such absorbent garments, the wearer's clothing covering the absorbent garments, such as pants, must generally be completely removed. Checking the status of the wearer's absorbent garment contents can be just as cumbersome as changing the absorbent garment.

Refastenable seams including mechanical fasteners, such as, for example, hook and loop fasteners, have been found to be particularly beneficial when used in conjunction with pant-like absorbent garments. Refastenable seams allow for the garment to be easily applied and removed, as well as periodically opened to check for exudates and closed if no exudates are found. Absorbent garments having elastic side panels or other non-refastenable side panels can have the side panels tucked into the center of the product for packaging purposes. Absorbent garments having refastenable side seams, on the other hand, can be prone to poor fastener performance if the side panels are tucked into the product in such a way as to cause creasing of a resilient fastening component.

When the refastenable side seam includes a resilient fastening component such as a hook component, these creases can deaden the hooks, thereby reducing the engageable area. As a result, a creased fastener tends to possess lower peel and/or shear values than uncreased fasteners. Products with severe and/or multiple fastener creases tend to be most apt to pop open during application and wear. Fastener creases appear to be more of an issue for hook components than for loop components due to the possibility of permanent deformation of hook material compared to the relative flexibility of loop material. A major cause of these performance-impairing creases is believed to be attributable to the manner and orientation in which the sides of the garments are tucked.

Certain automated processes exist in which the side panels are mechanically tucked into the garments along a conveyor prior to the garments reaching a stacking or accumulation device. In such processes, as the garment is being conveyed towards the stacker, mechanical blades rotate or travel with the product machine direction and push the side panels in from each side of the conveyor. The location of the mechanical blades is relied upon to control the location of the resulting folds. Alternatively, pneumatic forces, such as air bars are used to tuck the side panels. However, the location of the side panel folds is often inconsistent when such processes are used, thus resulting in creased fasteners.

Some process use vacuum to hold products on a conveyor, but the vacuum is applied effectively only at the center of the chassis, and at a moderate level, for example around 15 inches of water. Such use of a vacuum is not effective along the sides of the chassis.

There is a need or desire for a method of tucking side panels in which the location of the side folds can be controlled and the occurrence of damaged or creased fastening components can be reduced or eliminated.

SUMMARY OF THE INVENTION

In response to the discussed difficulties and problems encountered in the prior art, a new method of tucking refastenable side seams has been discovered.

The present invention is directed to a method of tucking a pair of opposing refastenable side seams into a body portion of a pant-like garment in which the fastening components can be positioned in a flat orientation and the location of the side panel folds can be controlled. The method involves the steps of positioning the body portion of the pant-like garment between an upper conveyor having an upper vacuum zone and a lower conveyor having a lower vacuum zone, with the refastenable side seams in a fastened position. The garment can be placed on the lower conveyor first, then moved along the lower conveyor toward the upper conveyor. The opposing vacuum forces from the upper and lower vacuum zones pull apart a front region of the body portion from a back region of the body portion. With the body portion in an open position, the side seams are pushed into the body portion towards one another, thereby creating longitudinal folds in the garment along outer longitudinal edges of the upper and lower vacuum zones. A pair of mechanical tucking blades can be used to push the side panels into the body portion.

The vacuum zones extend in the transverse direction, or cross machine direction, relative to the garment. The longitudinal edges of the vacuum zones determine the location of the longitudinal folds. The vacuum zone edges remain constant relative to the fold points of the side panels, thus producing consistent side panel folds. The vacuum zone edge remains constant at least through the tucking of the side panels and may be shut off later.

The tucking depth of the side portions can be controlled by the depth or height of the mechanical tucking blades, and the width of vacuum dead plates or a discrete vacuum hole pattern. During the tucking process, the mechanical tucking blades are suitably positioned either between the fastening component and the upper conveyor, or between the fastening component and the lower conveyor, to arrange the fastening components in a flat configuration in order to avoid causing any creases in the fastening components.

Once the side seams are tucked into the garment, the longitudinal folds can be held in place by reducing the gap between the upper and lower conveyors. The conveyors can run either parallel to one another or can be pivoted to reduce the exit gap between the conveyors. The garment can exit the upper conveyor and continue to process on top of the lower conveyor, using the same vacuum level and width ranges as used during the tucking process, to hold the fasteners down flat. After leaving the conveyors, the garment can be compressed with the fastening components lying flat within the body portion. The compressed garment can transferred to a stacker where the folds can be held in place, for example using stacker fingers or other suitable means.

With the foregoing in mind, it is a feature and advantage of the invention to provide a method of tucking refastenable side seams in which the fastening components can be positioned in a flat orientation and the location of the longitudinal folds can be controlled and consistent.

DEFINITIONS

Figure 1:
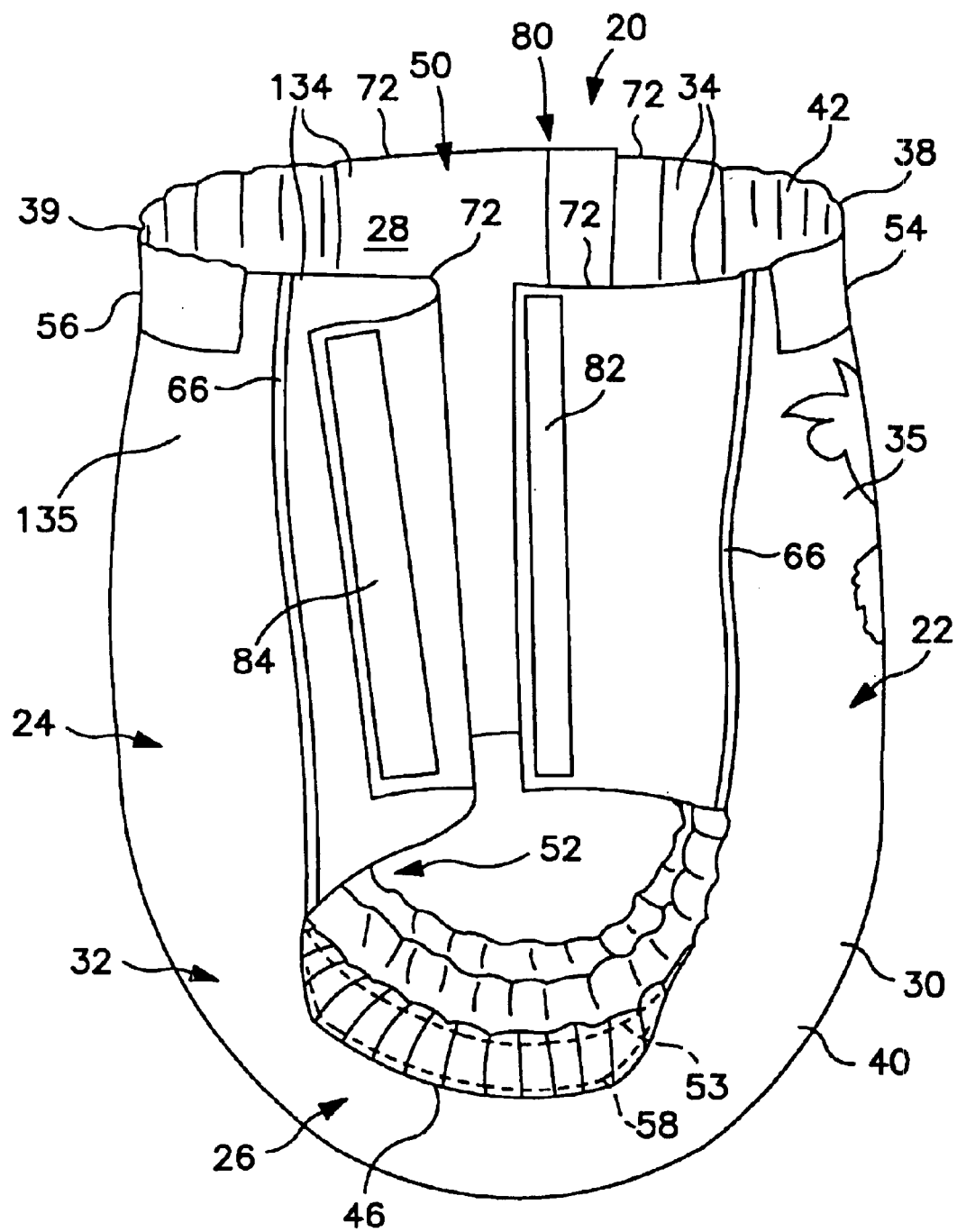
FIG. 1 is a perspective view of a training pant suitable for use in the present invention.

Within the context of this specification, each term or phrase below will include the following meaning or meanings.

"Attached" refers to the joining, adhering, connecting, bonding, or the like, of at least two elements. Two elements will be considered to be attached to one another when they are attached directly to one another or indirectly to one another, such as when each is directly connected to intermediate elements.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastomeric" and "elastic" refer to that property of a material or composite by virtue of which it tends to recover its original size and shape after removal of a force causing a deformation. It is generally preferred that the elastomeric material or composite be capable of being elongated by at least 50 percent, more preferably by at least 300 percent, of its relaxed length and recover, upon release of an applied force, at least 50 percent of its elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Flat" refers to an unfolded, or uncreased, configuration in which an element lies substantially in a single plane.

"Layer" when used in the singular can have the dual meaning of a single element or a plurality of elements.

"Liquid impermeable," when used in describing a layer or multilayer laminate, means that a liquid, such as urine, will not pass through the layer or laminate, under ordinary use conditions, in a direction generally perpendicular to the plane of the layer or laminate at the point of liquid contact.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Longitudinal" and "transverse" have their customary meaning, as indicated by the longitudinal and transverse axes depicted in FIGS. 3–10. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture. The refastenable elements can be attached, separated, and reattached for at least one cycle, suitably for at least 5 cycles, or suitably for at least 10 cycles.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Self-engaging fastener" refers to a fastening component that can engage with another fastening component having the same structure.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 250% of its initial length, desirably to at least 300% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Tucked" refers to a folded state of a garment in which at least one portion of the garment is inserted into the body portion to create a more compact orientation of the garment.

These terms may be defined with additional language in the remaining portions of the specification.

DETAILED DESCRIPTION OF THE PRESENTLY PREFERRED EMBODIMENTS

The present invention is directed to a method of tucking a pair of refastenable side seams into a body portion of a pant-like garment. The method allows the location of the side panel folds to be controlled and reduces the likelihood of creases occurring in the fastening components. A detailed description of the tucking process follows a description of the garment below.

The principles of the present invention can be used with any suitable pant-like garment, such as training pants, swim pants, diapers, incontinence products, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Referring to FIG. 1, a training pant 20 is illustrated in a partially fastened condition. The training pant 20 includes two refastenable seams 80, each extending from a waist opening 50 to one of two leg openings 52 on opposing sides of the garment 20. Each seam 80 includes a fastening component 82 and a mating fastening component 84. Either the fastening component 82 or the mating fastening component 84, or both, is a resilient fastening component. The term "resilient" as used herein refers to an interlocking material having a predetermined shape and the property of the interlocking material to resume the predetermined shape after being engaged and disengaged from a mating, complementary interlocking material. The resilient fastener may be deformed under great stress, such as during compression, particularly when the fastener does not lie in a flat plane. Resilient fastening components are typically formed from resilient material and have a backing and a plurality of engaging elements that project from the backing. An example of a suitable resilient fastening component is a hook type fastener that can repeatedly be engaged with and released from a loop type fastener.

It has been found that fastener performance can be compromised when a resilient fastening component in a refastenable seam is creased during tucking or compression in preparation for or during packaging. Usually, creases in fastening components formed during packaging and storage do not completely unfold or disappear during subsequent use of the garment. A crease or creases in a fastener hook component can deform individual hooks or the underlying material. The result of either deformation can be reduced engagement ability due either to deadened hooks or to spacing between hooks and loop material that prevent hooks from engaging in the loop material. When any hooks on a hook component are deadened, the engageable area of the hook component is reduced. As a result, a creased fastener tends to possess lower peel and/or shear values than uncreased fasteners. Products with severe and/or multiple fastener creases tend to be most apt to pop open during application and wear due to a greater number of deadened engagement elements. Creases can also hinder performance of fastener loop materials by flattening some of the loops, and by spacing some of the loops farther away from the hook material.

Fastener creases appear to be more of an issue for hook components than for loop components due to the potential permanent deformation of hook material compared to the relative flexibility of loop material. A major cause of these performance-impairing creases in refastenable seams is believed to be attributable to the orientation of the resilient fastening component before and/or during product compression, and before and/or during packaging. The tucked orientation of the refastenable seams 80 in the present invention prevents fastener creases from occurring, thus preserving the available fastener seam strength and making fasteners, such as hook and loop fasteners, less likely to disengage during product application and wear.

Referring again to FIG. 1, the training pant 20 includes a body portion 32 defining a front region 22, a back region 24, a crotch region 26 interconnecting the front and back regions, an inner surface 28 which is configured to contact the wearer, and an outer surface 30 opposite the inner surface which is configured to contact the wearer's clothing. The body portion 32 also defines a pair of longitudinally opposed waist edges, which are designated front waist edge 38 and back waist edge 39. The front region 22 is contiguous with the front waist edge 38, and the back region 24 is contiguous with the back waist edge 39. The body portion 32 also includes a pair of transversely opposed front side panels 34 and a pair of transversely opposed back side panels 134. The front and back side panels 34, 134 are formed along distal edges of the body portion and can either be integrally formed with the body portion, or can each include at least one separate element permanently attached to the body portion, as shown in FIG. 1. For reference, arrows 48 and 49 depicting the orientation of the longitudinal axis and the transverse axis, respectively, of the training pant 20 are illustrated in FIGS. 3–10.

The illustrated body portion 32 can include an outer cover 40, a bodyside liner 42 which is connected to the outer cover in a superposed relation, and an absorbent assembly (not shown) which is located between the outer cover 40 and the bodyside liner 42.

The fastening components can be either in the form of separate fastening components 82, as shown in FIG. 1, or in the form of fastening material forming at least a portion of the side panels 34 such that one fastening component on each side panel 34 can be releasably engaged with a mating fastening component incorporated into each back side panel 134. Similarly, the mating fastening components can be in the form of either separate mating fastening components 84, as shown in FIG. 1, or in the form of mating fastening material forming at least a portion of the back side panels 134. In various embodiments, either the entire outer cover 40 or the entire body side liner 42 or the front side panels 34 or the back side panels 134 can be made of a fastening material or a mating fastening material.

With the training pant 20 in the fastened position, as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34, 134 include the portions of the training pant 20 which, when worn, are positioned on the hips of the wearer.

As shown in FIG. 1, the front region 22 of the body portion 32 includes the transversely opposed front side panels 34 and a front panel 35 positioned between and interconnecting the side panels, along with a front waist elastic member 54 and any other connected components. The back region 24 of the body portion 32 includes the transversely opposed back side panels 134 and a back panel 135 positioned between and interconnecting the side panels, as well as a rear waist elastic member 56 and any other connected components.

The body portion 32 is configured to contain and/or absorb any body exudates discharged from the wearer. For example, the body portion 32 desirably, although not necessarily, includes a pair of containment flaps 46 which are configured to provide a barrier to the transverse flow of body exudates. A flap elastic member 53 can be operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can extend longitudinally along the entire length of the body portion 32 or may only extend partially along the length of the body portion. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include the front waist elastic member 54, the rear waist elastic member 56, and leg elastic members 58, as are known to those skilled in the art. The waist elastic members 54 and 56 can be operatively joined to the outer cover 40 and/or bodyside liner 42 along the opposite waist edges 38 and 39 as well as over waist edges 72 of the side panels 34, 134, and can extend over part or all of the waist edges. The leg elastic members 58 can be operatively joined to the outer cover 40 and/or bodyside liner 42 while longitudinally aligned along the distal edges and positioned in the crotch region 26 of the body portion 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally clothlike texture and/or mating fastening component qualities. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 may but need not have the same dimensions as the outer cover 40. The bodyside liner 42 is desirably compliant, soft feeling, and non-irritating to the child's skin. Further, the bodyside liner 42 can be less hydrophilic than the absorbent assembly, to present a relatively dry surface to the wearer and permit liquid to readily penetrate through its thickness. As mentioned, the bodyside liner 42 and/or the outer cover 40 can be made of a fastening component material or a mating fastening component material to eliminate the need for separately attached mating fastening components.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Uniqema, Inc., a division of ICI of New Castle, Del., and GLUCOPON® 220UP from Cognis Corp. of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly (not shown) is positioned between the outer cover 40 and the bodyside liner 42, which components can be joined together by any suitable means, such as adhesives, as is well known in the art. The absorbent assembly can be any structure which is generally compressible, conformable, non-irritating to the child's skin, and capable of absorbing and retaining liquids and certain body wastes. The absorbent assembly can be manufactured in a wide variety of sizes and shapes, and from a wide variety of liquid absorbent materials commonly used in the art. For example, the absorbent assembly can suitably include a matrix of hydrophilic fibers, such as a web of cellulosic fluff, mixed with particles of a high-absorbency material commonly known as superabsorbent material. High absorbency material can be provided in any form known in the art, including but not limited to particles, fibers, foams and films.

In a particular embodiment, the absorbent assembly includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonunifornly mixed. The fluff and superabsorbent particles can also be selectively placed into desired zones of the absorbent assembly to better contain and absorb body exudates. The concentration of the superabsorbent particles can also vary through the thickness of the absorbent assembly. Alternatively, the absorbent assembly can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly in an amount of from about 0 to about 90 weight percent based on total weight of the absorbent assembly. The absorbent assembly suitably has a density within the range of about 0.10 to about 0.50 grams per cubic centimeter. The absorbent assembly may or may not be wrapped or encompassed by a suitable tissue wrap that maintains the integrity and/or shape of the absorbent assembly.

The body portion 32 can also incorporate other materials that are designed primarily to receive, temporarily store, and/or transport liquid along the mutually facing surface with the absorbent assembly, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34, 134 disposed on each side of the body portion 32. These transversely opposed front side panels 34 and transversely opposed back side panels 134 can be permanently bonded to the front panel 35 and back panel 135 in the respective front and back regions 22, 24 along attachment lines 66, and are releasably attached to one another. The side panels 34, 134 may be permanently attached using attachment means known to those skilled in the art such as adhesive, thermal or ultrasonic bonding. As mentioned, the side panels 34, 134 can also be formed as continuous extensions of the front and back panels 35, 135.

The fastening components 82 can be permanently bonded to either the inner surface 28 or the outer surface 30 of each front side panel 34 adjacent each distal edge of the front region 22 of the body portion 32, and the mating fastening components 84 can be permanently bonded to either the inner surface 28 or the outer surface 30 of each back side panel 134 adjacent each distal edge of the back region 24 of the body portion, or either the inner surface 28 or the outer surface 30 of the body portion 32 can include fastening material or mating fastening material. The fastening components 82 and the mating fastening components 84 may be attached to the side panels 34 and the body portion 32 using attachment means known to those skilled in the art such as adhesive, thermal or ultrasonic bonding.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. In yet another embodiment, half of the fastening components 82 and half of the mating fastening components 84 can include hook type fasteners, while half of the fastening components 82 and half of the mating fastening components 84 can include loop type fasteners. In still another embodiment, each of the fastening components 82 and the mating fastening components 84 include self engaging fasteners. The fastening components 82 and the mating fastening components 84 are desirably rectangular, although they may alternatively be square, round, oval, curved, discontinuous such as multiple fasteners, or any other suitable shape. The fastening components 82 and mating fastening components 84 may or may not be parallel to a longitudinal midline of the garment 20.

In another embodiment, the nonwoven web in the outer cover 40 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In yet another embodiment, the nonwoven web in the bodyside liner 42 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In still another embodiment, an inner or outer surface of either the front side panels 34 or the back side panels 134 can include a loop-type fastening material, thereby eliminating the need for separate loop type fastening components 82 or 84.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. Suitable hook material can be molded or extruded of nylon, polypropylene or another suitable material. Suitable single-sided hook materials for the fastening components 82 or the mating fastening components 84 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

In particular embodiments for improved fit and appearance, the side panels 34, 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants 20 having an overall length dimension of about 54 centimeters, the side panels 34, 134 desirably have an average length dimension of about 10 centimeters or greater, such as about 15 centimeters.

The side panels 34 can include an elastic material capable of stretching in a direction generally parallel to the transverse axis 49 of the training pant 20. Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217

032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

Figure 2:
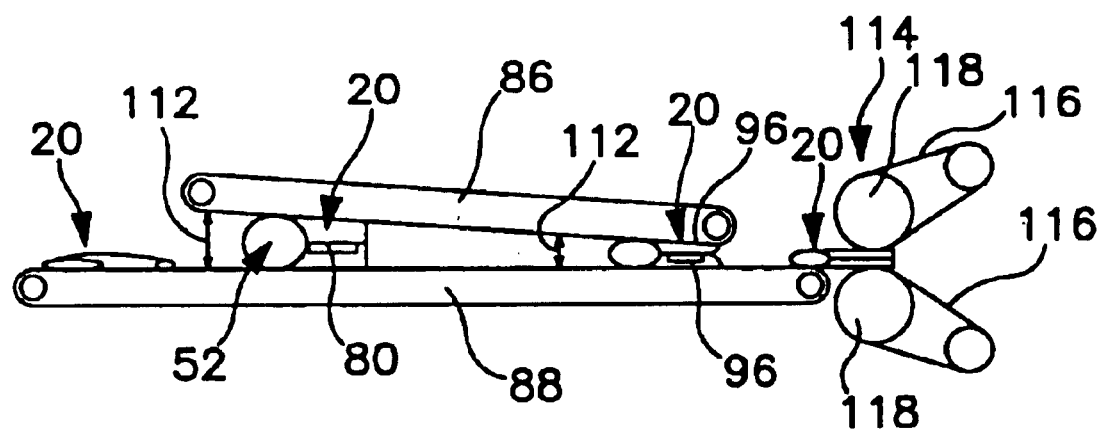
FIG. 2 is a side view of an arrangement of upper and lower vacuum conveyors and an infeed section.
Figure 3:
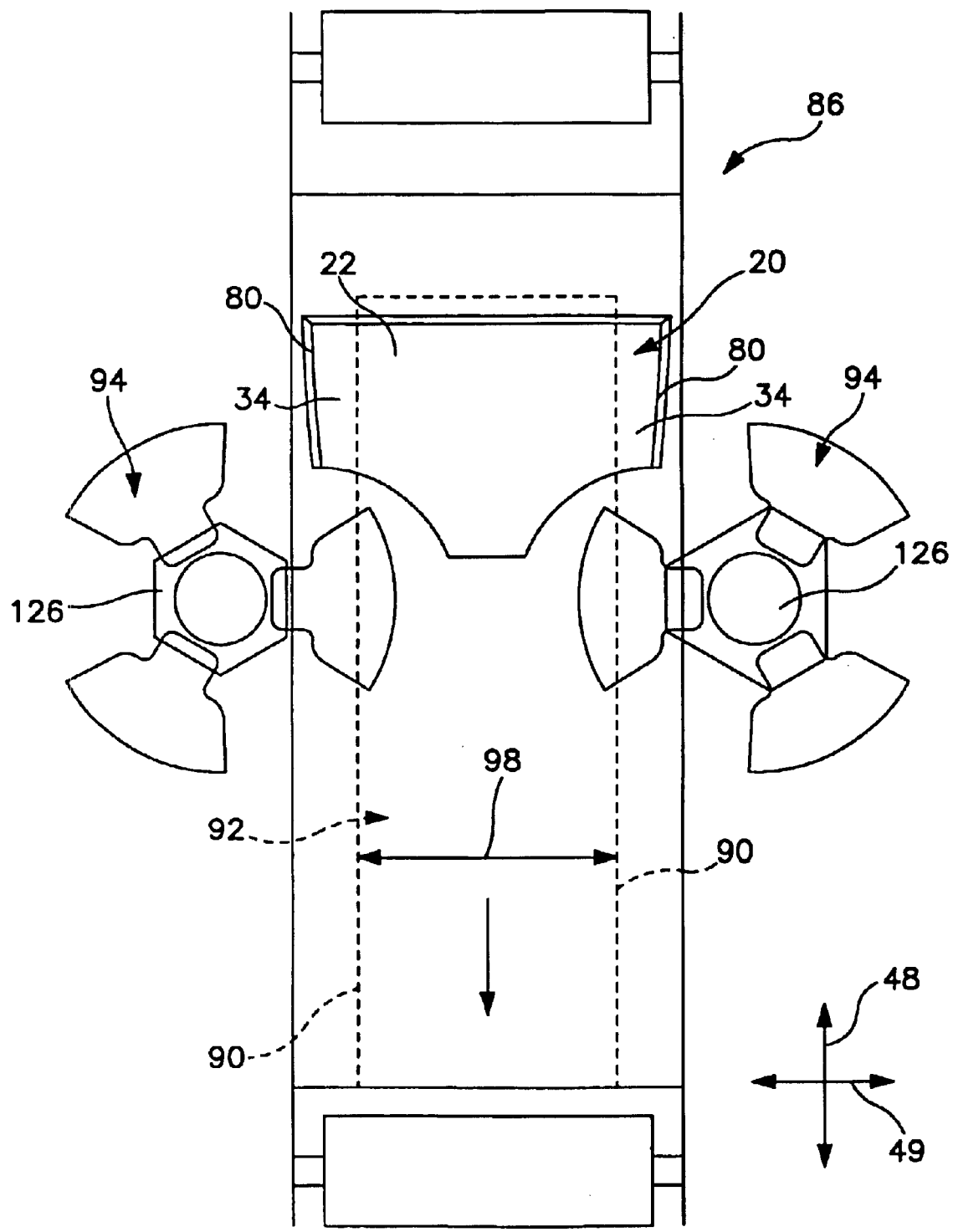
FIG. 3 is a top view of a conveyor.

In carrying out the method of the invention, the refastenable seams 80 are first pre-fastened, i.e., the fastening component 82 is releasably attached to the mating fastening component 84. Each refastenable seam 80 includes at least one resilient component. The training pant 20 is placed on top of a lower vacuum conveyor 88 with the fastened side seams 80 extended outward and suitably in a flat conformation, as shown in FIGS. 2 and 3. Either the front region 22 or the back region 24 can be facing up. The training pant 20 is moved along the lower conveyor 88 into alignment below an upper vacuum conveyor 86. As used herein, the term "conveyor" refers to either one conveyor or a series of conveyors acting in cooperation with one another. Vacuum zones 92 within the upper and lower conveyors 86, 88 pull the front region 22 and the back region 24 of the garment 20 apart from one another.

In another embodiment, only one of the conveyors 86, 88 has a vacuum zone 92. One conveyor, either an upper conveyor 86 or a lower conveyor 88, with a vacuum zone 92 may be sufficient to hold the training pant 20 in place during the method of the invention.

The vacuum zones 92 must be strong enough to maintain the training pant 20 in the open position with the front region 22 pulled apart from the back region 24. In order to do so, the vacuum zones 92 in both the upper and lower conveyors 86, 88 are suitably in a range of about 1 to about 100 inches of water. Alternatively, the vacuum zones 92 can be in a range of about 2 to about 50 inches of water, or from about 3 to about 35 inches of water. The vacuum zones 92 may also fall outside these ranges. For instance, materials that are less permeable would be expected to require less vacuum to hold them firmly in place while materials that are more permeable would be expected to require more vacuum to hold them firmly in place.

Figure 5:
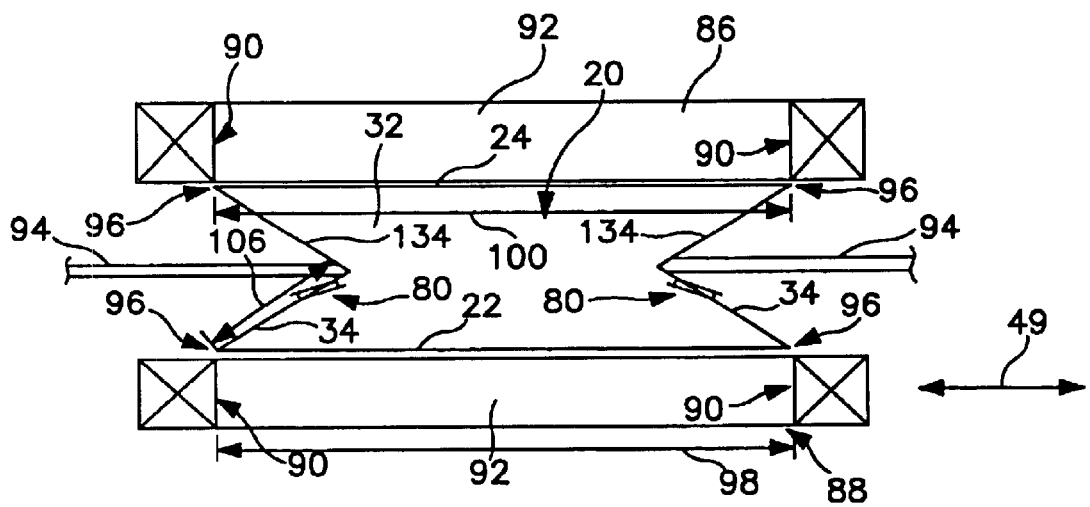
FIG. 5 is an end view of one embodiment of a training pant between upper and lower vacuum conveyors with side panels being tucked into the training pant.
Figure 6:
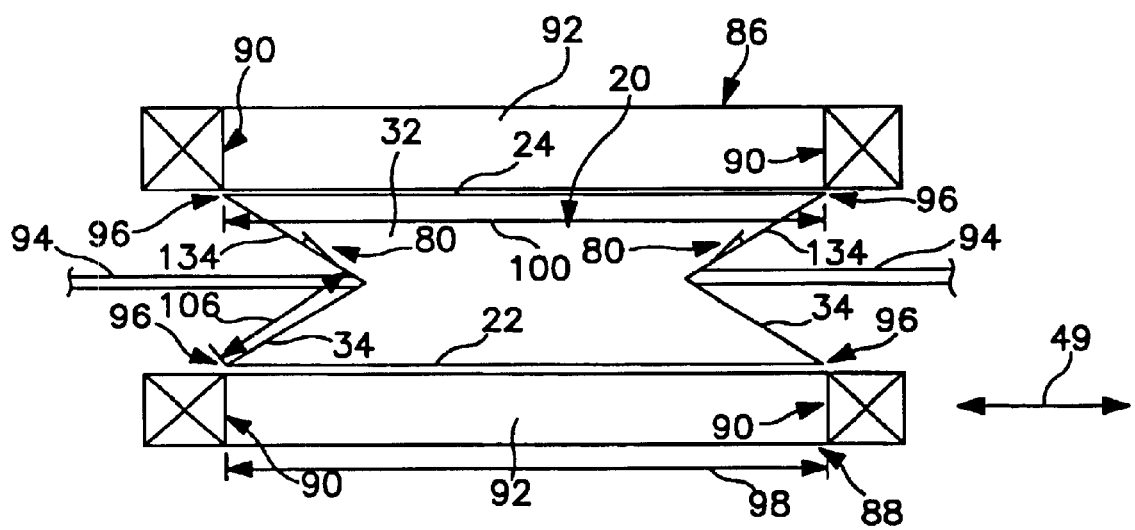
FIG. 6 is an end view of another embodiment of a training pant between upper and lower vacuum conveyors with side panels being tucked into the training pant.
Figure 7:
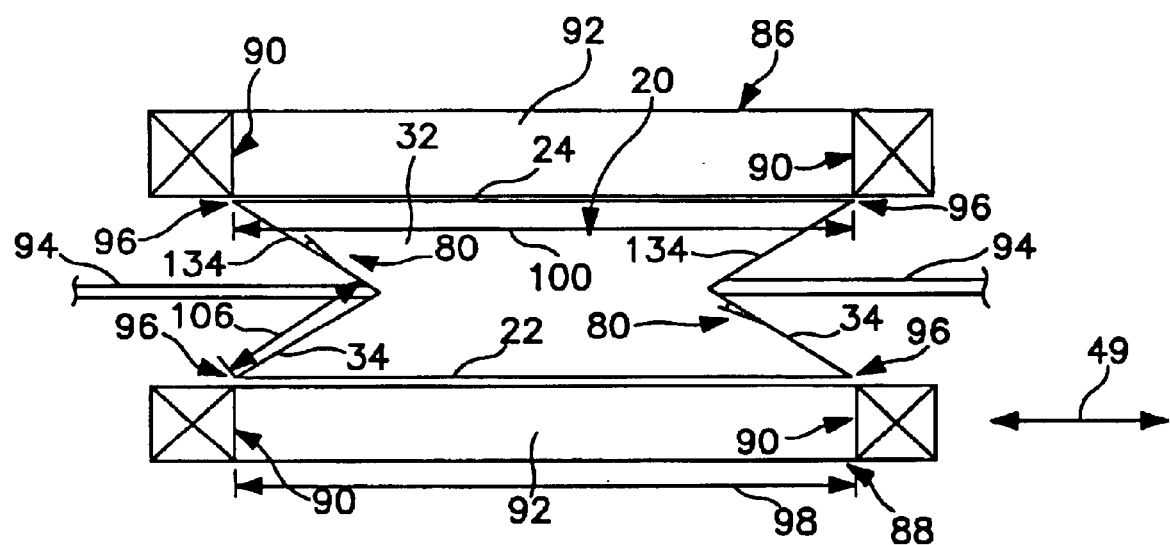
FIG. 7 is an end view of yet another embodiment of a training pant between upper and lower vacuum conveyors with side panels being tucked into the training pant.

The upper vacuum zone 92 and the lower vacuum zone 92 each have a transverse width 98 approximately equal to a desired folded transverse width 100 of the body portion of the pant 20, shown in FIGS. 5–7. For example, when using the method of the invention to fold a training pant, the width of the vacuum zone 92 on the lower conveyor 88 may be in a range of about 2 to about 12 inches wide. The width and vacuum of the lower conveyor 88 are designed to hold a desired width of either the front region or the back region of the body portion to the conveyor 88, allowing for a precise longitudinal fold 96 along the outer edges 90 of the lower vacuum zone 92. The width of the vacuum zone 92 on the upper conveyor 86 is suitably smaller than the width of the vacuum zone 92 on the lower conveyor 88, for example in a range of about 1 to about 7 inches wide for a training pant. Like the lower conveyor 88, the width and vacuum of the upper conveyor 86 are designed to hold a desired width of either the front region or the back region of the body portion to the conveyor 86, allowing for a precise longitudinal fold 96 along the outer edges 90 of the upper vacuum zone 92.

Once the pant 20 is open, the side seams 80 can be tucked into the body portion 32 of the pant, as shown in FIGS. 4–7, using a pair of mechanical tucking blades 94 to push the side seams 80 inward a certain distance 106 toward one another. The mechanical tucking blades 94 are used to push the side panels 34 into the training pant 20 such that the longitudinal folds 96 are at the outer, longitudinal edges 90 of the vacuum zones 92, as shown in FIGS. 5–7. The mechanical tucking blades 94 are suitably positioned either between the side seam 80 and the vacuum zone 92 of the upper conveyor 86, as shown in FIG. 5, or between the side seam 80 and the vacuum zone 92 of the lower conveyor 88, as shown in FIG. 6, or between one of the side seams 80 and the vacuum zone 92 of the upper conveyor 86 and between one of the side seams 80 and the vacuum zone 92 of the lower conveyor 88, as shown in FIG. 7, in each instance pushing the side seam 80 into a flat configuration.

Figure 4:
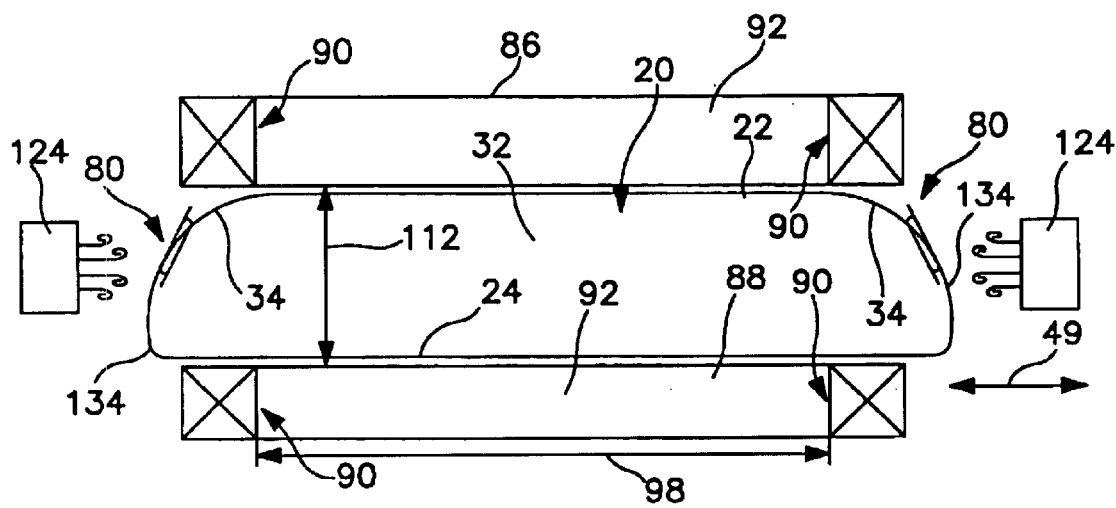
FIG. 4 is an end view of a training pant between upper and lower vacuum conveyors.

In another embodiment of the invention, a pair of opposing air bars 124 can be used to blow the side seams 80 inward after the training pant 20 has been opened but before the tucking blades 94 push the side seams 80 inward, thereby possibly aiding the performance of the invention. An illustration of this step is shown in FIG. 4.

Figure 8:
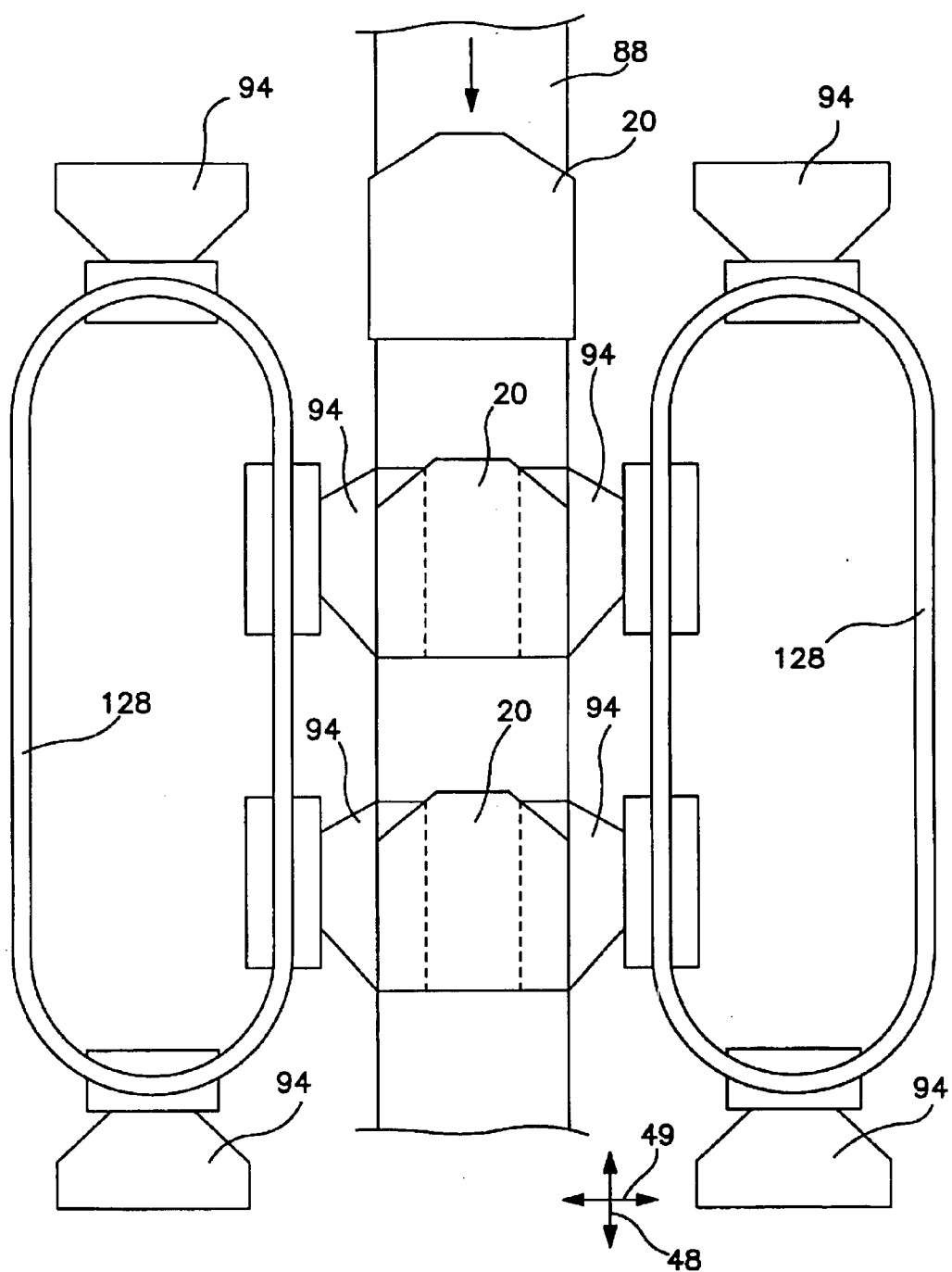
FIG. 8 is a top view of a conveyor between two tracks that guide mechanical tucking blades.
Figure 9:
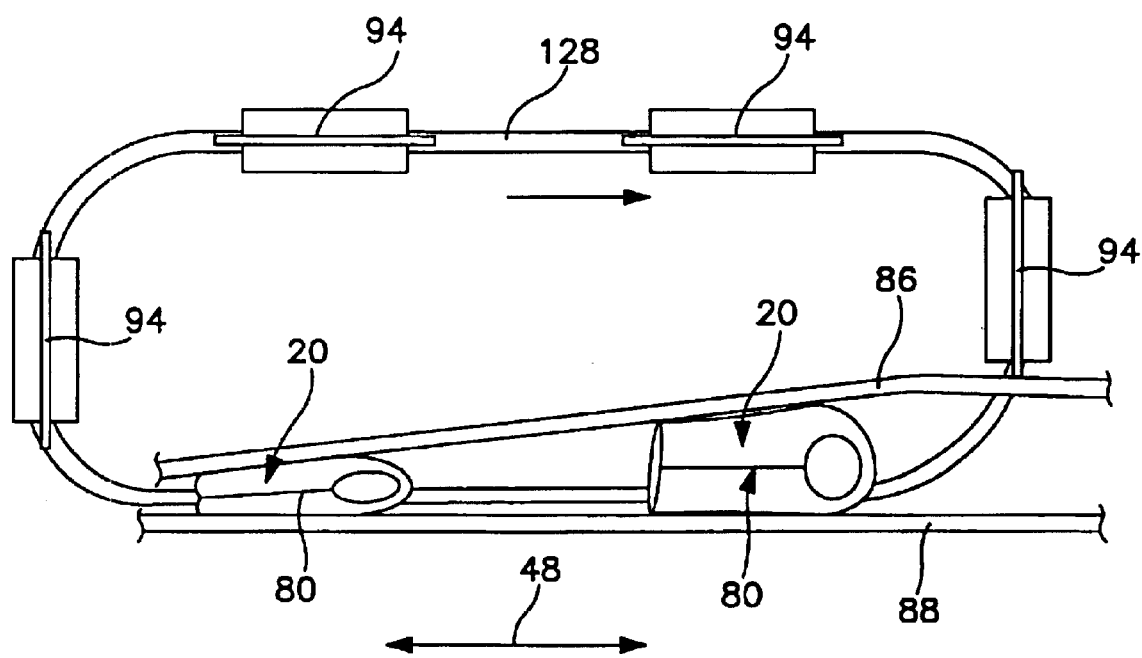
FIG. 9 is a side view of a track that guides mechanical tucking blades adjacent a conveyor.
Figure 10:
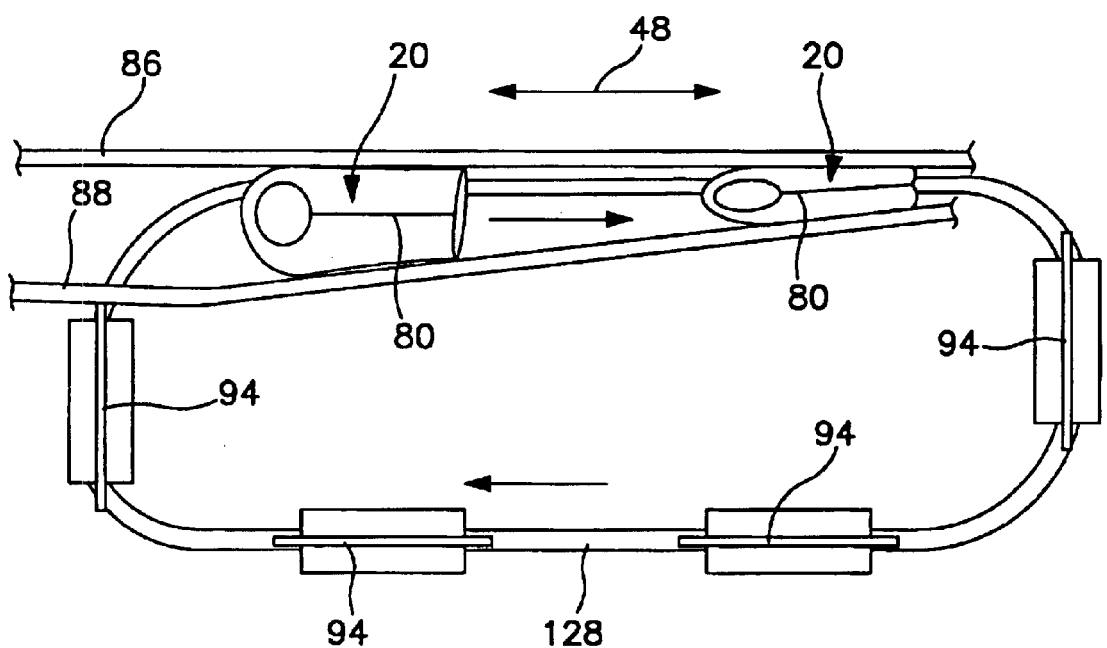
FIG. 10 is a side view of another track that guides mechanical tucking blades adjacent a conveyor.

Examples of suitable mechanical tucking blades 94 include mechanical tucking blades 94 on a rotary paddle 126, as shown in FIG. 3. In other embodiments, shown in FIGS. 8, 9, and 10, the path of a track 128 that guides the mechanical tucking blades 94 can be designed so that the mechanical tucking blades 94 travel with the pant 20 over a longer path length than with a rotary paddle. The mechanical tucking blades 94 can be held essentially parallel to the track path 128 and travel generally in the plane of the folded pant 20, as shown in FIG. 8. Alternatively, the mechanical tucking blades 94 can be held at an angle to the track path 128 and travel both in the plane of the folded pant 20 and above it, as shown in FIG. 9, or below it, as shown in FIG. 10. By using a track 128 designed in this manner, the mechanical tucking blades 94 can match the speed of travel of the pant 20 for a longer time. For example, the speed of a tucking blade 94 in the machine direction depends on the point of rotation of the rotary paddle 126, with the speed being fastest when the tucking blade 94 is at closest approach to the pant 20. Also, because a tucking blade 94 on a track 28 can have fall contact of its outer edge with the panels 34, 134 of the pant, a straight-edge tucking blade 19 can be used.

A tucking blade 94 used in any mechanical tucking device in the method of the invention can have an optimized shape so that a tail end of the tucking blades 94 does not knock the fold out of place. An example of an optimized shape is a circular blade 94 having cut-out portions, as shown in FIG. 3. Also, different sizes and/or shapes of tucking blades 94 can be used for products of different sizes. A tucking blade 94 can also be shaped or adapted to provide unequal tucking of front versus back panels, or waist edge of the panel versus leg edge.

Figure 11:
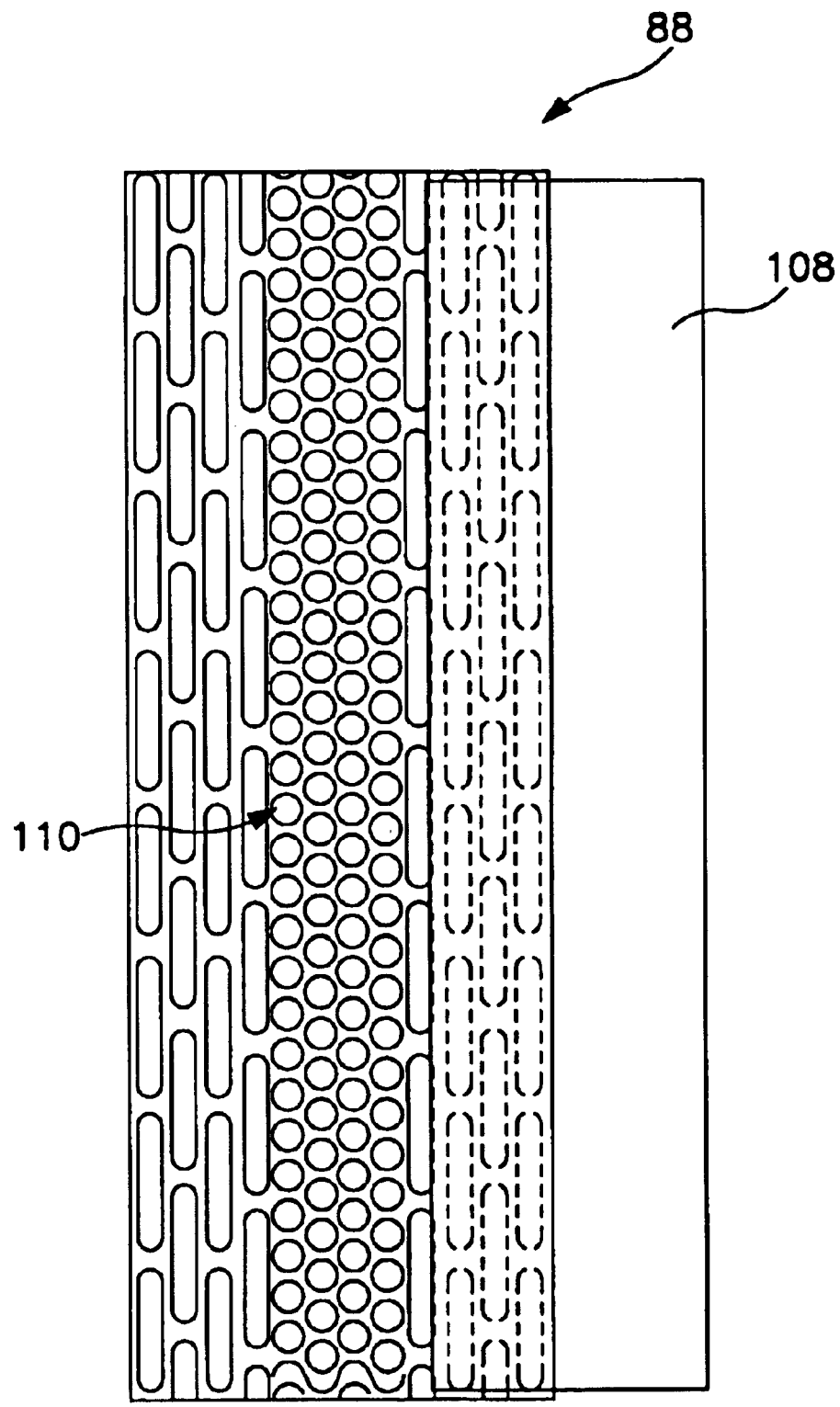
FIG. 11 is a top view of a vacuum zone having a discrete vacuum hole pattern and a vacuum dead plate.

The tucking depth of the side seams 80 can be controlled by the depth and height of the mechanical tucking blades 94, as shown in FIGS. 5–7, and/or by the width of vacuum dead plates 108 or a discrete vacuum hole pattern 110 on the conveyors 86, 88, as shown in FIG. 11. The tucking blades 94 can vary in shape, size and thickness to produce the desired tuck. In one embodiment of the invention, the vacuum zones 92 can be shifted to the right or left of the machine centerline to adapt for any weave that may be present in the product path.

The location of the longitudinal folds 96 is determined by the transverse width 98 of the vacuum zones 92 of the conveyors 86, 88. The longitudinal folds 96 occur at about the longitudinal edges 90 of the vacuum zones 92, as shown in FIGS. 4–7. Since the transverse width 98 of the vacuum zones 92 remains constant, the locations of the longitudinal folds 96 are fairly consistent from product to product.

Figure 12:
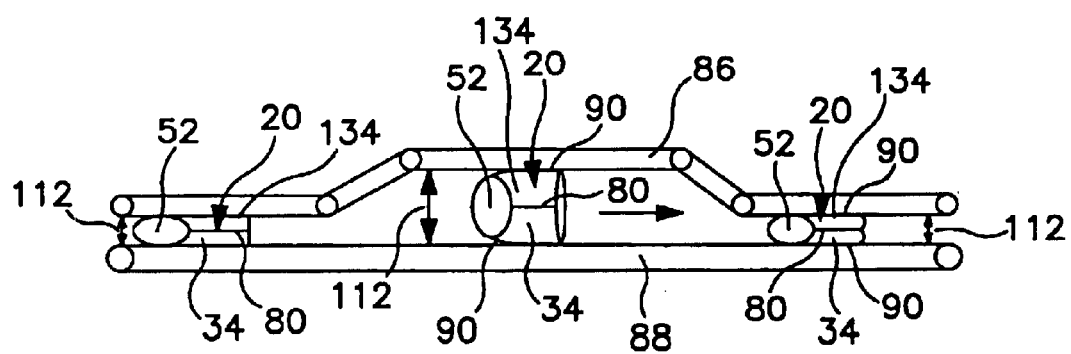
FIG. 12 is a side view of an arrangement of upper and lower vacuum conveyors.

The conveyors 86, 88 can run either parallel to one another, or can be pivoted, as shown in FIG. 2. Once the side seams 80 are tucked into the body portion 32, the longitudinal folds 96 may be held in place by reducing the distance 112 between the upper and lower conveyors 86, 88. The upper and lower conveyors 86, 88 may converge either at the same time the side seams 80 are being tucked or after the side seams 80 have been tucked. An entry gap, or distance 112, between the conveyors 86, 88 can range from about 1.5 to about 3.25 inches, or suitably from about 2 to about 3 inches. An exit gap, or distance 112, between the conveyors 86, 88 can range from about 0.75 to about 3.25 inches, or from about 1 to about 2.5 inches. The training pant 20 can exit the upper conveyor 86 first, as shown in FIG. 2, and continue to process on top of the lower conveyor 88 using the same vacuum level and width ranges, described above, to hold the side seams 80 down flat. Alternatively, the upper and lower conveyors 86, 88 may initially diverge, thereby increasing the distance 112 between the conveyors 86, 88 to permit panel tucking, then converge again, as shown in FIG. 12.

Figure 13:
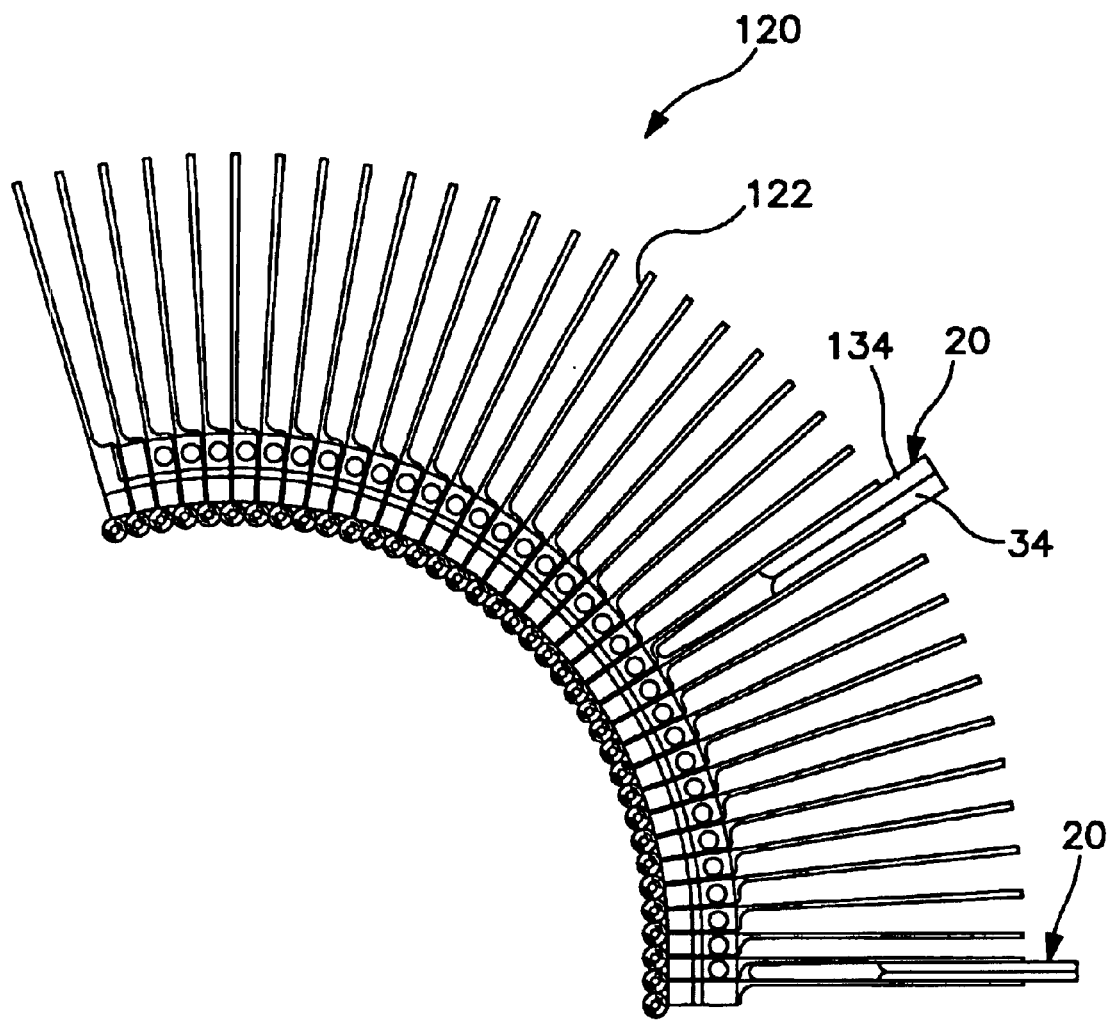
FIG. 13 is a plan view of a stacker.

The training pant 20 can then be transferred from the lower conveyor 88 to an infeed section 114, suitably made up of several belts 116 and nip rolls 118, as shown in FIG. 2. The infeed section 114 compresses the pant with the side seams 80 lying flat within the body portion 32 and holds the side seams 80 in a flat configuration until the pant enters an accumulation device, such as a stacker 120. The compressed pant 20 enters the stacker 120 where consecutive stacker finger units 122 hold the pant 20 closed and the longitudinal folds 96 in place, as shown in FIG. 13.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of tucking a pair of opposing, refastenable side seams into a body portion of a pant-like garment, each refastenable side seam including at least one resilient component, the method comprising the steps of:
   positioning the body portion of the pant-like garment on a conveyor having a vacuum zone, with the refastenable side seams in a fastened position wherein the vacuum zone has a transverse width about equal to a desired folded transverse width of the body portion in contact with the vacuum zone;
   holding the body portion on the conveyor using vacuum force from the vacuum zone;
   pushing the refastenable side seams into the body portion a distance toward one another while the vacuum force is holding the body portion on the conveyor, creating longitudinal folds in the garment along outer longitudinal edges of the vacuum zone; and
   compressing the garment with each of the at least one resilient components pushed into the body portion and in a flat conformation.

2. The method of claim 1, wherein the vacuum zone has a vacuum in a range of between about 1 inch of water and about 100 inches of water.

3. The method of claim 1, wherein the vacuum zone has a vacuum in a range of between about 2 inches of water and about 50 inches of water.

4. The method of claim 1, wherein the vacuum zone has a vacuum in a range of between about 3 inches of water and about 35 inches of water.

5. The method of claim further comprising the step of using a plurality of mechanical tucking blades to push the opposing side seams into the body portion toward one another.

6. The method of claim 5, further comprising the step of using the mechanical tucking blades to control the distance the refastenable side seams are pushed into the body portion toward one another.

7. The method of claim 1, further comprising the step of using vacuum dead plates to control the distance the refastenable side seams are pushed into the body portion toward one another.

8. The method of claim 1, further comprising the step of using a pair of opposing mechanical tucking blades, each mechanical tucking blade positioned between the conveyor and one of the side seams, to push the opposing side seams into the body portion toward one another.

9. The method of claim 1, further comprising the step of using a pair of opposing mechanical tucking blades to push the opposing side seams into the body portion toward one another, with each of the side seams positioned between one of the mechanical tucking blades and the conveyor.

10. The method of claim 1, further comprising step of using a pair of opposing mechanical tucking blades to push the opposing side seams into the body portion toward one another, with one of the mechanical tucking blades positioned between the conveyor and one of the side seams, and one of the side seams positioned between one of the mechanical tucking blades and the conveyor.

11. The method of claim 1, further comprising the step of inserting the garment between two consecutive stacker finger units subsequent to pushing the opposing side seams into the body portion toward one another.

12. A method of tucking a pair of opposing, refastenable side seams into a body port on of a pant-like garment, each refastenable side seam including at least one resilient component, the method comprising the steps of:
   positioning the body portion of the pant-like garment between an upper conveyor having an upper vacuum zone and a lower conveyor having a lower vacuum zone, with the refastenable side seams in a fastened position, wherein the upper vacuum zone has a transverse width about equal to a desired folded transverse width of the body portion in contact with the upper vacuum zone and the lower vacuum zone has a transverse width about equal to a desired folded transverse width of the body portion in contact with the lower vacuum zone;
   holding apart front region of the body portion from a back region of the body portion using opposing vacuum forces from the upper and lower vacuum zones;
   pushing the refastenable side seams into the body portion a distance toward one another while the opposing vacuum forces are holding apart the front region of the body portion from the back region of the body portion, creating longitudinal folds in the front and back regions of the garment along outer longitudinal edges of the upper and lower vacuum zones; and compressing the garment with each of the at least one resilient components pushed into the body portion and in a flat conformation.

13. The method of claim 12, further comprising the step of using a plurality of mechanical tucking blades to push the opposing side seams into the body portion toward one other.

14. The method of claim 12, further comprising the step of using a pair of opposing mechanical tucking blades, each mechanical tucking blade positioned between the upper conveyor and one of the side seams, to push the opposing side seams into the body portion toward one another.

15. The method of claim 12, further comprising the step of using a pair of opposing mechanical tucking blades, each mechanical tucking blade positioned between the lower conveyor and one of the side seams, to push the opposing side seams into the body portion toward one another.

16. The method of claim 12, further comprising the step of using a pair of opposing mechanical tucking blades to push the opposing side seams into the body portion toward one another, with one of the mechanical tucking blades positioned betweentheupper conveyor and one of the side seams, and one of the mechanical tucking blade positioned between the lower conveyor and one of the side seam.

17. The method of claim 12, further comprising the step of directing a pair of opposing air bars toward the opposing side seams prior to pushing the opposing side seams into the body portion toward one another.

18. The method of claim 12, further comprising the step of reducing a distance between the upper conveyor and the lower conveyor subsequent to pushing the opposing side seams into the body portion toward one another.

19. The method of claim 12, further comprising the step of reducing a distance between the upper conveyor and the lower conveyor while pushing the opposing side seams into the body portion toward one another.

20. The method of claim 12, further comprising the step of inserting the garment between two consecutive stacker finger units subsequent to pushing the opposing side seams into the body portion toward one another.

21. The method of claim 12, wherein the pant-like garment comprises a training pant.

22. The method of claim 12, wherein the pant-like garment comprises a swim pant.

\* \* \* \* \*

UNITED STATES PATENT AND TRADEMARK OFFICE
CERTIFICATE OF CORRECTION

PATENT NO.   : 6,776,316 B2
DATED        : August 17, 2004
INVENTOR(S)  : Van Eperen et al.

It is certified that error appears in the above-identified patent and that said Letters Patent is hereby corrected as shown below:

Title page,
Item [75], Inventors, the address for "Steven James Langolf" should be -- Fond du Lac --.

Column 16,
Line 13, add -- 1 -- after "The method of claim" and before "comprising the step of".
Line 35, add -- the -- after "further comprising" and before "step of".
Line 47, replace "port on" with -- portion --.
Line 61, add -- a -- after "holding apart" and before "front region".

Column 17,
Line 24, replace "betweentheupper" with -- between the upper --.

Column 18,
Line 1, replace "blade" with -- blades --.
Line 2, replace "seam" with -- seams --.

Signed and Sealed this

Eighth Day of February, 2005

JON W. DUDAS
*Director of the United States Patent and Trademark Office*